United States Patent [19]

van der Stoel et al.

[11] Patent Number: 4,599,421
[45] Date of Patent: Jul. 8, 1986

[54] PROCESS FOR THE PREPARATION OF A PYRIDONE-2

[75] Inventors: Roland E. van der Stoel, Buchten; Marcel A. R. Bosma, Geleen, both of Netherlands

[73] Assignee: Stamicarbon B.V., Geleen, Netherlands

[21] Appl. No.: 601,342

[22] Filed: Apr. 17, 1984

[30] Foreign Application Priority Data

Apr. 22, 1983 [NL] Netherlands ......................... 8301416

[51] Int. Cl.$^4$ ............................................. C07D 211/88
[52] U.S. Cl. ..................................... 546/251; 546/250
[58] Field of Search ................................. 546/250, 251

[56] References Cited

FOREIGN PATENT DOCUMENTS 53-18580  2/1978  Japan .................................... 546/250

Primary Examiner—Alan L. Rotman
Attorney, Agent, or Firm—Cushman, Darby & Cushman

[57] ABSTRACT

Pyridone-2 compounds are prepared by reacting an oxoalkanecarboxylic acid having as general formula

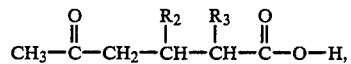

where $R_2$ and $R_3$ represent hydrogen or an alkyl group having 1–4 C atoms, or an ester of such an acid in the gas phase with an amine compound $R_1NH_2$, where $R_1$ represents hydrogen or an alkyl group with 1–4 C atoms, at a temperature of 250°–450° C. in the presence of a dehydrogenating catalyst.

8 Claims, No Drawings

PROCESS FOR THE PREPARATION OF A PYRIDONE-2

The invention relates to a process for the preparation of a pyridone-2. Such a process is known from the Japanese patent application 18580-1978. In that publication 5-oxocaproic acid amides are started from, which amides are converted in one dehydrating and also dehydrogenating step into 6-methylpyridone-2 compounds by means of a catalyst. The starting compound is prepared by reaction between acetone or methylethylketone and acrylamides or methacrylamides. These reactions take place under elevated pressure, about 20 bar at 200° C. Consequently, the synthesis of the starting compound is relatively expensive. The object of the invention lies in a process for the preparation of a pyridone-2 which is commercially attractive.

According to the present invention an oxoalkanecarboxylic acid having as general formula:

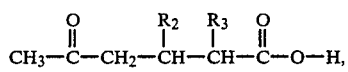

where $R_2$ and $R_3$ represent hydrogen or an alkyl group having 1–4C atoms, or an ester of such an acid is reacted in the gas phase with an amine compound $R_1NH_2$,
where $R_1$ represents hydrogen or an alkyl group having 1–4C atoms, at a temperature of 250°–450° C. in the presence of a dehydrogenating catalyst, and a pyridone-2 having as general formula

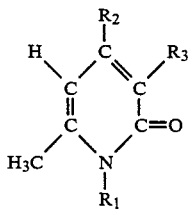

where $R_1$, $R_2$ and $R_3$ have the meanings described above, is recovered from the resulting mixture.

The reaction according to the invention can be carried out with dehydrogenating catalysts known in the art, for instance a metal or compound of a metal from the 8th group or 1st auxiliary group of the periodic system of the elements according to Mendeleeff. Very suitable are palladium-containing catalysts. These catalyst are often applied on a supporting material. Suitable supporting materials for use in the process according to the invention are, for instance, activated carbon, graphite, silicon oxide, aluminium oxide, magnesium oxide and mixtures of these materials.

The process according to the invention can be carried out at various temperatures, for instance temperatures in the range of 250°–450° C. Preference is given to using a temperature of 270°–350° C.

The reaction according to the invention is carried out while using ammonia or a primary amine. The quantity of ammonia or primary amine can be varied, for instance between 1 and 20 moles per mole starting compound. Application of a quantity larger than 20 moles ammonia or primary amine per mole starting compound is possible, but the result achieved then is not better. Preference is given to using 1–10 moles ammonia or primary amine per mole starting compound. If a primary amine is used, the resulting reaction product is an N-substituted pyridone having on the N atom a substituent corresponding with the primary amine used. Any primary amine that can be present under the reaction conditions in a gaseous state can be used. The primary amine or the ammonia need not be added as such, but can be formed also in situ by reduction of another compound, for instance by reduction of a nitro compound to primary amine or of a hydrazine to ammonia.

If the reaction is carried out in the temperature range of 270°–350° C., it is an advantage to use hydrogen in the reaction mixture, because the activity of the catalyst can then be maintained at a high value for a long time. The quantity of hydrogen can be varied, for instance between 0.01 and 10 moles, preferably 0.1–5 moles hydrogen per mole starting compound. More than 10 moles hydrogen per mole starting compound can be used also, but the quantity of pyridone-2 then decreases in consequence of the formation of byproducts, such as piperidone-2.

The process according to the invention can be carried out very effectively in the presence of an inert diluent such as, for instance, nitrogen (in addition to any hydrogen used). A regular evaporation of liquid starting compound can then be achieved.

As starting product various oxoalkanecarboxylic acids or esters of these acids can be used. The process according to the invention is very suitable for the conversion of oxoalkanecarboxylic acids or esters of these acids with 3 carbon atoms in the carbon chain between the carbon atom of the carbonyl group and the carbon atom of the carboxyl group such as, for instance, 5-oxocaproic acid or esters of this acid.

Preference is given to using an ester of the said acids as starting product, because a yield can then be obtained higher than that obtained in the application of the acid as such. The resulting byproduct in applying the ester is an alcohol corresponding with the ester group. Various ester groups can be used such as, for instance, a methyl, ethyl and isopropyl group.

For the practical realization of the process according to the invention the modes of realization for gas phase reactions known per se may be applied, for instance the modes of realization in which the gaseous starting mixture is passed over the catalyst in the form of fixed bed or so-called fluid bed. The space velocity may be varied, for instance between 0.001 and 2 g starting compound per milliliter catalyst material (bulk volume) per hour.

By cooling the resulting gaseous reaction mixture a condensate can be obtained from which the desired pyridone-2 can be recovered by, for instance, crystallization or distillation.

The compounds obtained in the process according to the invention can be used in the preparation of crop protection chemicals.

The invention is further elucidated in the following examples.

EXAMPLES I–IV

Through a vertical tubular reactor, diameter 25 millimeters, length 400 millimeters, containing a zone of 50 milliliters (bulk volume) catalyst and provided with a heating jacket, a gaseous mixture of methyl 5-oxocaproate, ammonia, hydrogen and nitrogen is passed from top to bottom for 75 hours. The catalyst is bounded at the top and bottom by inert ceramic material. The gaseous mixture is obtained by evaporation of liquid methyl 5-oxocaproate in a flow of gaseous ammonia, hydrogen and nitrogen. Per mole methyl 5-oxocaproate, 0.6 mole hydrogen, 3 moles ammonia and 5 moles nitrogen are used. The temperature in the reactor is kept at 310° C. The catalyst used is palladium on γ-aluminium oxide promoted with sodium (catalyst with 1.0% (wt) Pd and 0.6% (wt) Na).

Per ml (bulk volume) catalyst 0.10 g oxoester is passed through per hour.

After 2, 26, 50 and 74 hours of operation the quantity of methyl 5-oxocaproate passed through and the quantity of reaction product (after condensing the latter at 5° C.) are measured for 1 hour.

The quantity of methyl 5-oxocaproate passed through is determined by measuring the loss in weight of liquid methyl 5-oxocaproate. The composition of the reaction product is determined gaschromatographically. From this determination of the weight of the quantity of methyl 5-oxocaproate passed over in the relative period of 1 hour the conversion of the oxo-ester and the yield of 6-methylpyridone-2 can be calculated.

The conversion is understood to mean the quantity of oxo-ester converted (quantity of oxo-ester passed over less the quantity of oxo-ester in the condensed product) expressed as a percentage of the quantity of oxo-ester passed over. The yield of 6-methylpyridone-2 is understood to mean the quantity of 6-methylpyridone-2 in the condensed product expressed as a percentage of the quantity of 6-methylpyridone-2 that can theoretically be formed from the quantity of oxo-ester converted.

The results are summarized in table I.

TABLE I

| Example | hrs of operation | conversion % | yield % |
|---|---|---|---|
| I | 2 | 100 | 66 |
| II | 26 | 96 | 77 |
| III | 50 | 93 | 82 |
| IV | 74 | 92 | 85 |

EXAMPLE V

In the manner described in examples I–IV, a mixture of 5-oxocaproic acid, ammonia, hydrogen and nitrogen is passed over the catalyst for 4 hours. In this process a 100% conversion of the 5-oxocaproic acid and a 71% yield of 6-methylpyridone-2 were measured.

EXAMPLES VI–VII

In the manner described in examples I–IV, methyl 5-oxocaproate is reacted at a temperature of 300° C., in which process the space velocity is 0.20 g ester per milliliter catalyst per hour. Per mole ester, 0.5 mole hydrogen, 2 moles ammonia and 4 moles nitrogen are used.

The results are summarized in table II.

TABLE II

| Example | hrs of operation | conversion % | yield % 6-methylpyridone-2 |
|---|---|---|---|
| VI | 4 | 94 | 60 |
| VII | 45 | 79 | 73 |

EXAMPLE VIII

In the manner described in examples I–IV, methyl 5-oxocaproate is converted at a temperature of 320° C. After 24 hours of operation a 97% conversion of methyl 5-oxocaproate and a 65% yield of 6-methylpyridone-2 are measured.

EXAMPLE IX

In the manner described in examples I–IV, methyl 5-oxocaproate is converted at a temperature of 300° C. The space velocity is 0.15 g ester per milliliter catalyst per hour. As catalyst 0.5% Pd/0.4% Na on γ-alumina is used. Per mole ester, 1 mole hydrogen, 3 moles ammonia and 5 moles nitrogen are metered. After 26 hours of operation the conversion is 87% and the yield of 6-methylpyridone-2 52%.

We claim:

1. Process for the preparation of a pyridone-2, wherein an oxoalkanecarboxylic acid having as general formula

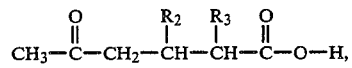

where $R_2$ and $R_3$ represent hydrogen or an alkyl group having 1–4C atoms, or a $C_1$ to $C_3$ lower alkyl ester of such an acid is reacted in the gas phase with an amine compound $R_1NH_2$, where $R_1$ represents hydrogen or an alkyl group with 1–4C atoms, at a temperature of 250°–450° C. in presence of a dehydrogenating catalyst which is a metal or compound of a metal from the 8th group or 1st auxiliary group of the periodic system of elements according to Mendeleef, to form a pyridone-2 having as general formula

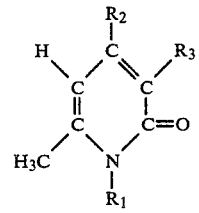

where $R_1$, $R_2$ and $R_3$ have the meanings described above.

2. Process according to claim 1, wherein the starting compound used is an ester of an oxoalkanecarboxylic acid.

3. Process according to claim 1, wherein a palladium-containing dehydrogenating catalyst is used.

4. Process according to claim 1, wherein the reaction is carried out while applying 1-10 moles ammonia or primary amine per mole starting compound.

5. Process according to claim 1, wherein the reaction is carried out at a temperature of 270°-350° C.

6. Process according to claim 5, wherein the reaction is carried out in the presence of 0.1-5 moles hydrogen per mole starting compound.

7. Process according to claim 1, wherein the reaction is carried out in the presence of inert diluent.

8. Process according to claim 1, wherein the starting compound used is 5-oxocaproic acid methyl ester.

* * * * *